United States Patent [19]
Wilk

[11] Patent Number: 5,511,564
[45] Date of Patent: *Apr. 30, 1996

[54] LAPAROSCOPIC STRETCHING INSTRUMENT AND ASSOCIATED METHOD

[75] Inventor: Peter J. Wilk, New York, N.Y.

[73] Assignee: Valleylab Inc., Boulder, Colo.

[*] Notice: the term of this patent shall not extend beyond the expiration date of Pat. No. 5,318,013.

[21] Appl. No.: 382,280

[22] Filed: Feb. 1, 1995

Related U.S. Application Data

[63] Continuation of Ser. No. 154,809, Nov. 18, 1993, Pat. No. 5,395,367, which is a continuation-in-part of Ser. No. 922,165, Jul. 29, 1992, Pat. No. 5,312,391, and Ser. No. 972,508, Nov. 6, 1992, Pat. No. 5,318,013.

[51] Int. Cl.$^6$ ..................................................... A61B 19/00
[52] U.S. Cl. ........................... 128/898; 606/1; 600/201
[58] Field of Search ........................... 128/3, 20, 898; 606/1, 51, 52, 110, 190, 191, 198, 205–211; 600/201, 204, 207

[56] References Cited

U.S. PATENT DOCUMENTS

| | | | |
|---|---|---|---|
| 3,834,392 | 9/1974 | Lampman et al. | 128/4 |
| 4,432,352 | 2/1984 | Wineland | 606/208 |
| 4,655,219 | 4/1987 | Petruzzi | 606/206 |
| 4,686,965 | 8/1987 | Bonnet et al. | 128/4 |
| 4,700,694 | 10/1987 | Shirhido | 128/4 |
| 4,732,163 | 3/1988 | Bonello et al. | 604/280 |
| 4,924,851 | 5/1990 | Ognier et al. | 604/264 |
| 5,099,827 | 3/1992 | Melzer et al. | 606/142 |
| 5,144,942 | 9/1992 | Decarie et al. | 128/4 |
| 5,275,608 | 1/1994 | Forman et al. | 606/170 |
| 5,318,013 | 6/1994 | Wilk | 128/20 |
| 5,402,772 | 4/1995 | Moll et al. | 128/20 |

FOREIGN PATENT DOCUMENTS

| | | | |
|---|---|---|---|
| 0035357 | 3/1930 | France | 606/208 |
| 0015314 | 8/1908 | United Kingdom | 606/198 |

Primary Examiner—Stephen C. Pellegrino
Assistant Examiner—Glenn Dawson
Attorney, Agent, or Firm—R. Neil Sudol; Henry D. Coleman

[57] ABSTRACT

A surgical device includes a frame member having a distal end and a proximal end and a pair of tissue holding mechanisms movably mounted to the frame member at the distal end thereof for securing holds on spaced organic tissues of a patient. Actuators mounted to the frame member at the proximal end thereof are operatively connected to the holding mechanisms for controlling the operation thereof. Another actuator, also mounted to the frame member, is operatively connected to the holding mechanisms for moving the holding mechanisms relative to one another, thereby stretching organic tissues between the held tissues and facilitating access to the stretched tissues. The instrument assembly is particularly useful during laparoscopic surgery.

7 Claims, 5 Drawing Sheets

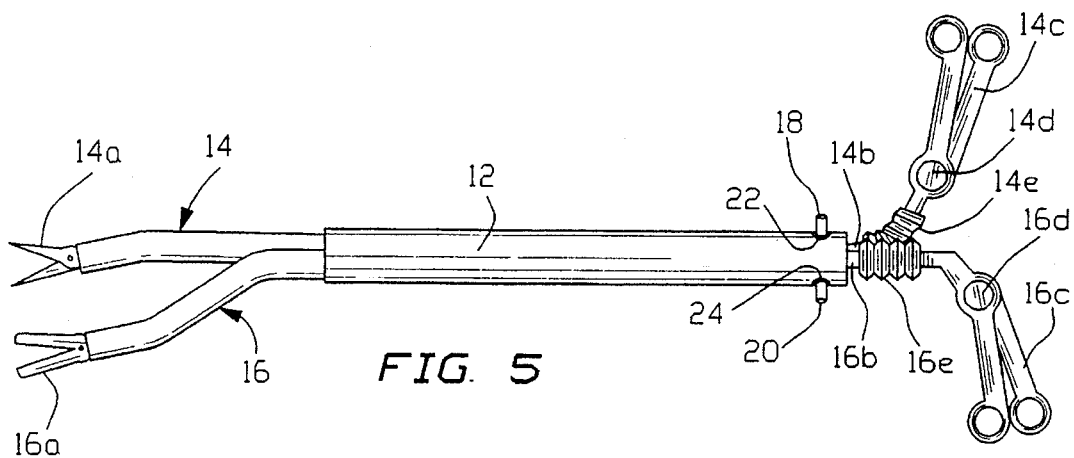
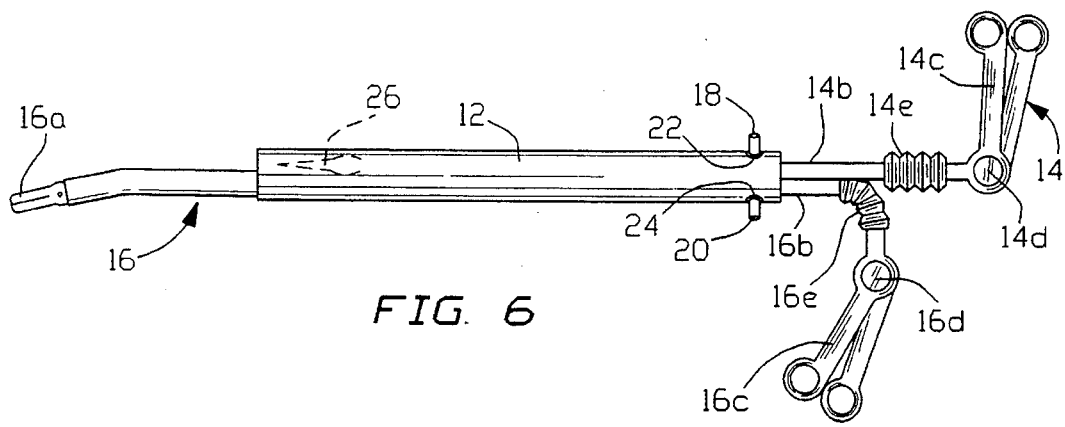
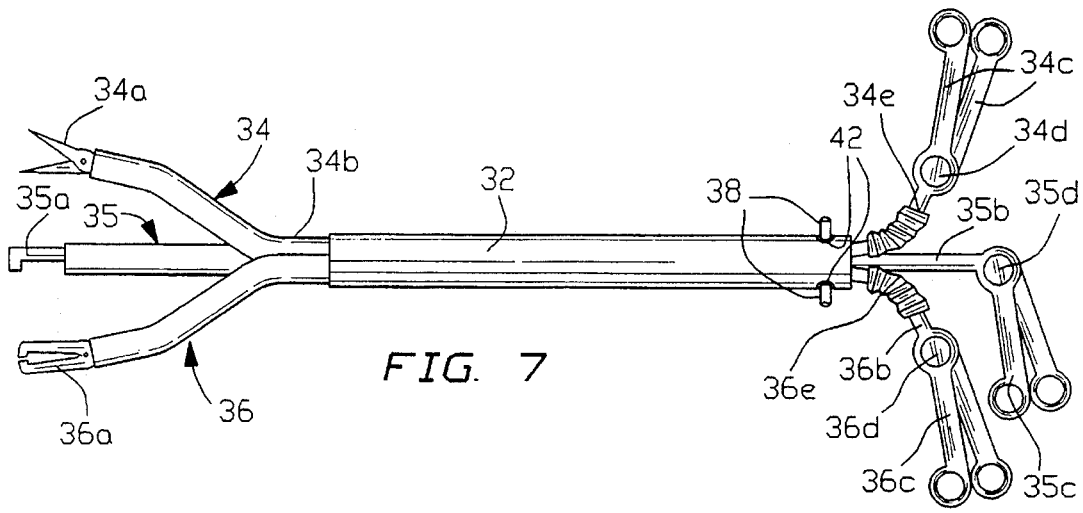

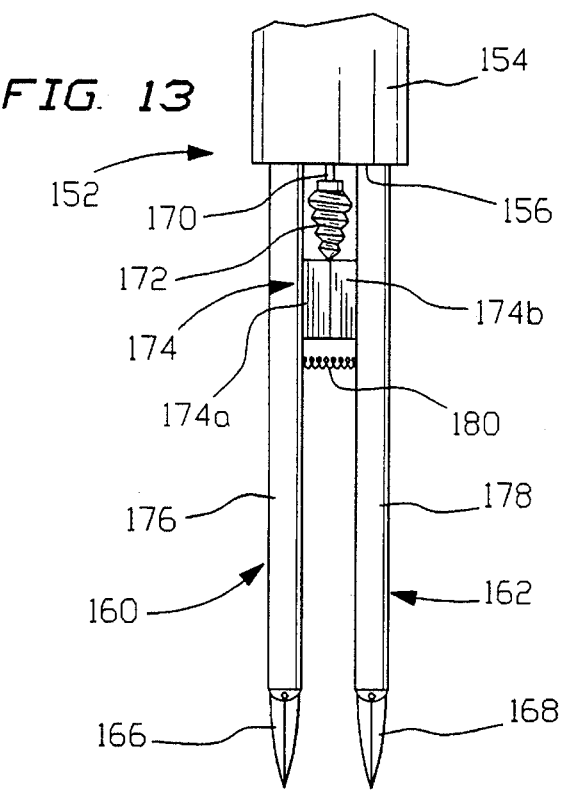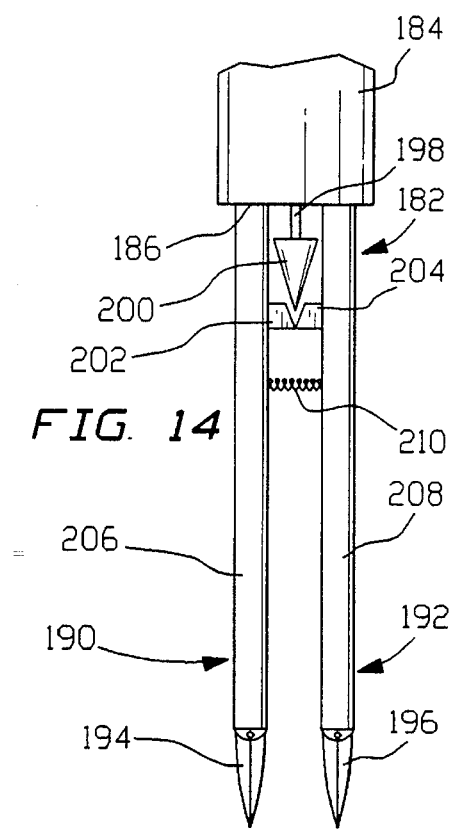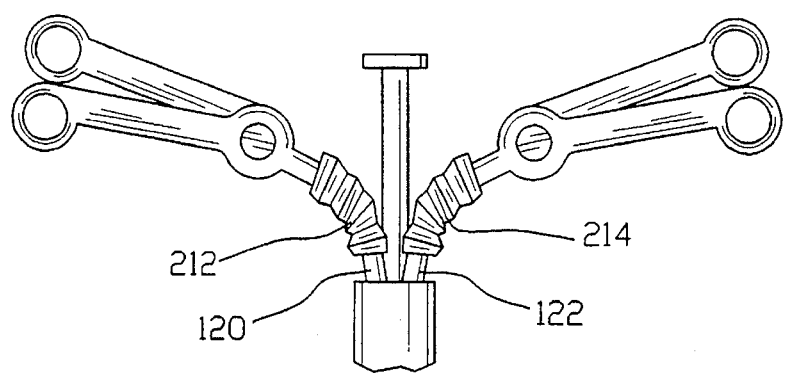

LAPAROSCOPIC STRETCHING INSTRUMENT AND ASSOCIATED METHOD

CROSS-REFERENCE TO RELATED APPLICATIONS

This application is a continuation of application Ser. No. 08/154,809, filed Nov. 18, 1993 and issued as U.S. Pat. No. 5,395,367, which is a continuation-in-part of U.S. patent application Ser. No. 07/922,165, filed Jul. 29, 1992, now U.S. Pat. No. 5,312,391, and U.S. patent application Ser. No. 07/972,508, filed Nov. 6, 1992, now U.S. Pat. No. 5,318,013.

BACKGROUND OF THE INVENTION

This invention relates to a laparoscopic instrument assembly. This invention also relates to a method for use in laparoscopic surgery.

Laparoscopy involves the piercing of the abdominal wall and the insertion of a tubular port member or laparoscopic cannula through the perforation. Various instruments may be inserted through the tubular member to perform surgical operations inside the abdomen.

Generally, upon the disposition of the first cannula or trocar sleeve so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Generally, laparoscopic surgery is performed with rigid instruments, the distal end portions of which are inserted into the patient's abdominal cavity through one or more tubular port members inserted in perforations formed in the abdominal wall. To enable the different laparoscopic surgical instruments to reach different locations within the abdominal cavity, the tubular cannulas are tilted or pivoted.

In a more recent development, the distal terminal portions of some laparoscopes are flexible and bendable under control of the surgeon by the manipulation of actuator members outside the patient. As in endoscopic surgery, surgical instruments such as biopsy forceps, graspers, trocars, suction devices, irrigators, scissors, cautery devices, staplers, suture applicators and clamps, may be inserted through one or more longitudinal channels in the laparoscopes or endoscopes. These instruments are at least partially flexible to enable them to flex with the bending type motions of the laparoscopes or endoscopes in which they are inserted.

It frequently occurs during laparoscopic surgery that an additional instrument is temporarily required. Inserting this extra instrument has usually involved either temporarily removing one of the other instruments or forming another perforation with a trocar. However, inasmuch as trocar manufacturers are marketing torcar sleeves of increasing large diameter, the possibility exists for introducing more than one instrument through the same laparoscopic cannula or port member. This possible procedure entails certain problems with respect to manipulating a plurality of instruments at essentially the same location.

A particular laparoscopic surgical procedure and associated instrument assembly is disclosed in U.S. patent application Ser. No. 07/972,508. That application is directed to an improved laparoscopic procedure and instrument for spreading convoluted and folded organic tissues to enable visual inspection and physical access to a potential surgical site. Generally, such access is conventionally achieved by initially attaching a first clamp to tissues on one side of the desired site and a second clamp to tissues on the opposite side of the site. The clamps are then pulled apart, by surgical assistants, to spread the tissues between the two clamps. This conventional procedure, although useful and effective in open surgery, is cumbersome in laparoscopic surgery, and could be streamlined.

OBJECTS OF THE INVENTION

An object of the present invention is to provide a device and an associated method for facilitating laparoscopic surgery.

A more particular object of the present invention is to provide a laparoscopic instrument assembly and/or an associated method which facilitates the utilization of an increased number of instruments without increasing the number of perforations in a patient's abdomen.

Another particular object of the present invention is to provide such an instrument assembly and or an associated surgical procedure which facilitates the performance of an operation by making a plurality of laparoscopic surgical instruments more readily manipulable by surgeon.

Yet another, specific object of the present invention is to provide such a surgical instrument assembly for use in spreading organic tissues of a patient during an operation.

These and other objects of the present invention will be apparent from the drawings and detailed descriptions herein.

SUMMARY OF THE INVENTION

A laparoscopic surgical device comprises, in accordance with the present invention, a laparoscopic instrument shaft having a distal end and a proximal end, an operative tip capable of performing a surgical operation and disposed at the distal end of the shaft, and a manually operable actuator provided at the proximal end of the shaft for actuating the operative tip, the actuator having an axis oriented at an angle with respect to the shaft. A connector element is provided for connecting the actuator to the shaft so that the orientation of the actuator with respect to the shaft can be varied prior to the performance of an operation with the operative tip. The modification of the actuator orientation can be effectuated prior to or upon an insertion, into a patient during a laparoscopic operation, of a distal end portion of the device including the operative tip of the shaft.

According to another feature of the present invention, the shaft is one of a plurality of laparoscopic instrument shafts each having a distal end and a proximal end, each of the shafts being provided at its respective distal end with a respective operative tip capable of performing a surgical operation. In this case, the laparoscopic device further comprises a frame such as a rigid sleeve which permanently connects the shafts in parallel to one another. Accordingly, the shafts are together insertable through an opening in a patient's skin surface during a laparoscopic operation. At least a given one of the shafts may be slidably mounted to the sleeve for sliding motion relative thereto. A lock may be provided on the sleeve and the given shaft for alternately locking that shaft in a retracted neutral position and an extended use position.

According to a further feature of the present invention, the actuator is one of a plurality of manually operable actuators provided at the proximal ends of respective ones of the shafts for independently actuating the respective operative tips. Each of the actuators has a respective axis oriented at a variable angle with respect to the shafts.

According to yet another feature of the present invention, a length modification component is connected to at least a selected one of the shafts for varying a distance of the respective actuator from the selected shaft. The length modification component may include a telescoping shaft section. This length modification component, particularly where the multiple instrument shafts are fixed with respect to one another, serves to provide more space for the surgeon's hands. It is equivalent in that sense to a sliding instrument shaft.

According to an additional feature of the present invention, the laparoscopic instrument or device further comprises means for removably attaching one or more of the actuators to the respective shafts so that the actuators can be selectively replaced with different actuators. Of course, the replaceable handles are preferably locked in some way to the instrument shafts. This locking may be accomplished simply by a force lock fit or may be accomplished via spring loaded latched or detents. The replacement actuators may have different dimensions, e.g., for accommodating surgeons having differently sized hands, or other different operational characteristics.

In order to enable an adjustment in the orientation of an actuator or handle with respect to a respective instrument shaft, the connector may include a bendable shaft section disposed at the proximal end of the shaft, between the shaft and the actuator. The bendable shaft section may take the form of a bellows type spring tube as in common use in drinking straws for children.

Where each of a pair of shafts is provided at its respective distal end with respective clamping jaws and a frame permanently connects the shafts in parallel to one another so that the shafts are together insertable through an opening in a patient's skin surface during a laparoscopic operation, the actuator is one of a plurality of manually operable actuators provided at the proximal ends of the respective shafts for independently actuating the clamping jaws. The connector connects the actuators to the respective shafts so that the orientations of the actuators with respect to the shafts can be varied prior to a laparoscopic operation. This embodiment of the invention also comprises a stretching mechanism mounted to the frame and operatively connected to the clamping jaws for increasing a distance between the clamping jaws to thereby stretch organic tissues held by the clamping means.

A laparoscopic surgical method in accordance with the present invention utilizes a laparoscopic instrument shaft having an operative tip at a distal end and a manually operable actuator at a proximal end for actuating the operative tip, the shaft being connected to the actuator so that an orientation of the actuator with respect to the shaft can be varied. The method comprises the steps of (a) forming a perforation in an external skin surface of a patient, (b) inserting, into the patient through the perforation, a distal end portion of the instrument shaft including the operative tip, (c) exerting a manual force on the actuator to change the orientation of the actuator with respect to the shaft, and (d) manipulating the actuator to operate the operative tip to perform a surgical operation on tissues inside a patient. Changing the orientation of the actuator with respect to the shaft may be effectuated prior to or after insertion of the instrument into the patient.

Pursuant to an alternative or additional feature of the present invention, the actuator is removably connected to the shaft, while the method further comprises the steps of removing the actuator from the shaft and attaching another actuator to the shaft.

Where the actuator includes an actuator handle connected to the instrument shaft via a length modification component, the method further comprises the step of operating the length modification means to vary the distance of the handle from the shaft. Again, this length adjustment may be performed prior to or after the insertion of the laparoscopic instrument into the patient.

Where the shaft is a first one of a plurality of laparoscopic instrument shafts each provided at a respective distal end with a respective operative tip and a frame is provided for permanently connecting the shafts in parallel to one another, the insertion of the instrument shaft includes the step of inserting all of the shafts together through the perforation.

The method may further comprise the step of sliding the first shaft relative to the frame prior to the manipulation of the actuator to operate the operative tip to perform the surgical operation. The slidable shaft may be locked to the shaft and unlocked therefrom prior to the sliding step. Subsequently, the shifted shaft is again locked to the frame upon completion of the sliding step.

Pursuant to another feature of the present invention, where the actuator is one of a plurality of manually operable actuators provided at the proximal ends of respective ones of the shafts, the method further comprises the step, executed subsequently to the step of manipulating, of manipulating another actuator to operate another one of the surgical tips to perform another surgical operation.

Where the length modification means includes a locking element, the actuator is unlocked from the shaft prior to the operation of the length modification means to change the distance of the actuator from the respective shaft.

Where the connector includes a bendable shaft section disposed at the proximal end of the shaft, between the shaft and the actuator, the changing of the orientation of the actuator relative to the shaft is implemented by bending the bendable shaft section.

Where the shaft is one of a pair of shafts each provided at a respective distal end with a respective clamping mechanism for exerting a clamping force on organic tissues of a patient, and the laparoscopic instrument further comprises a frame for permanently connecting the shafts in parallel to one another, the insertion of the instrument into the patient includes the step of inserting the shafts together through the perforation. Further steps comprise operating the clamping mechanisms to clamp organic tissues of a patient at spaced points and increasing a distance between the clamping mechanisms and concomitantly the spaced points, thereby stretching organic tissues between the spaced points. Where the shafts are flexible at their distal ends, the increasing in the interclamp distance is effectuated by pressing the shafts apart from one another.

Another laparoscopic surgical method in accordance with the present invention comprises the steps of (i) providing a laparoscopic instrument shaft having an operative tip at a distal end and a manually operable actuator provided at a proximal end of the shaft for actuating the operative tip, (ii) forming a perforation in an external skin surface of a patient, (iii) inserting, into the patient through the perforation, a distal end portion of the instrument shaft including the operative tip, (iv) removing the actuator from the shaft, (v) attaching a different actuator to the shaft at the proximal end thereof, and (vi) manipulating the actuator to operate the operative tip to perform a surgical operation on tissues inside a patient. The steps of removing the first actuator and attaching the replacement may be performed subsequently to or prior to the insertion of the distal end portion of the instrument into the patient.

A laparoscopic device and an associated method in accordance with the present invention facilitate laparoscopic surgery by providing greater maneuvering space for the hands of the surgeon(s). The bendable shafts enable a surgeon to separate dual actuators at a single laparoscopic cannula by a comfortable distance. Accordingly, each instrument can be customized to the individual physician. Moreover, this ergonomic customization in use can be accomplished or modified during the surgery itself, depending, for example, on the fatigue of the surgeon and more importantly on the particular surgical site and operation to be performed.

Accordingly, the present invention facilitates the utilization of an increased number of instruments without increasing the number of perforations in a patient's abdomen. The performance of an operation is facilitated by making a plurality of laparoscopic surgical instruments more readily manipulable by a surgeon. An example of a specific laparoscopic operation which benefits by the present invention is the spreading organic internal tissues of a patient.

BRIEF DESCRIPTION OF THE DRAWING

FIG. 5 is a schematic side elevational view, on a reduced scale, of another laparoscopic instrument or device in accordance with the present invention, showing the assembly in one operational state.

FIG. 6 is a schematic side elevational view of the laparoscopic instrument of FIG. 1, showing the instrument in a different operational state.

FIG. 7 is a schematic side elevational view, on a reduced scale, of another laparoscopic instrument or device in accordance with the present invention.

FIG. 13 is a partial schematic side elevational view of another laparoscopic surgical clamping assembly, showing a pair of grasping forceps disposed in a mutually parallel insertion configuration and with closed grasping jaws.

FIG. 14 is a partial schematic side elevational view of yet another laparoscopic surgical clamping assembly, showing two grasping forceps parallel to one another insertion configuration and with closed grasping jaws.

FIG. 15 is a partial schematic side elevational view of a modification to the laparoscopic surgical clamping assemblies of FIGS. 10–14, in accordance with the present invention.

DETAILED DESCRIPTION

Figure 1:
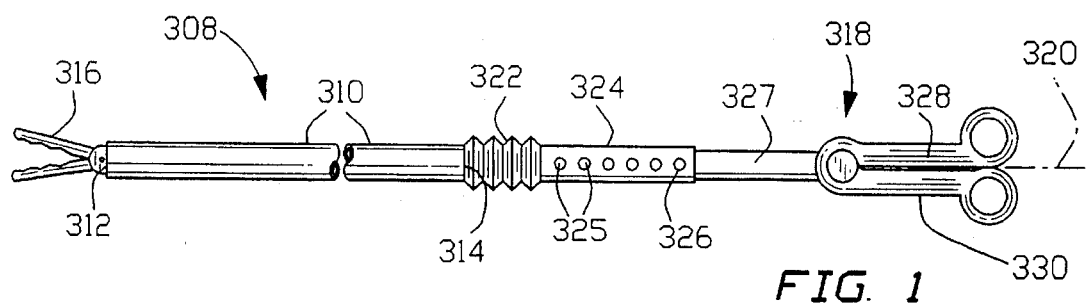
FIG. 1 is a schematic side elevational view, on a reduced scale, of a laparoscopic instrument device in accordance with the present invention, showing the assembly in one operational state.
Figure 2:
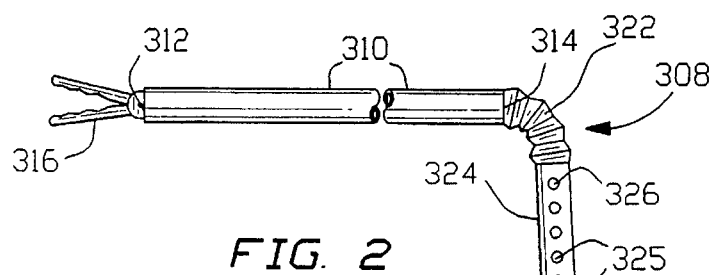
FIG. 2 is a schematic side elevational view of the laparoscopic instrument assembly of FIG. 1, showing the assembly in a different operational state.

As illustrated in FIGS. 1 and 2, a laparoscopic surgical device 308 comprises a laparoscopic instrument shaft 310 having a distal end 312 and a proximal end 314. An operative tip 316 in the form of a pair of clamping jaws capable of performing a surgical operation is disposed at the distal end 312 of shaft 310, while a manually operable actuator 318 is provided at the proximal end 314 of shaft 310 for actuating operative tip 316. Actuator 318 has an axis 320 oriented at an angle (0° in FIG. 1 and 90° in FIG. 2) with respect to shaft 310. A connector element 322 connects actuator 318 to shaft 310 so that the orientation of actuator 318 with respect to shaft 310 can be varied prior to the performance of an operation with operative tip 316. The orientation of actuator 318 may be changed prior to after an insertion of a distal end portion of device 308 into a patient during a laparoscopic operation.

Connector element 322 takes the form of a bellows or accordion-like element which is stable in any of a plurality of different angles. Such a structure is found in children's drinking straws.

Connector element 322 may take any form which allows adjustment of the angle between shaft 310 and axis 320 upon the application of a manual force to device 308. For example, shaft 310 and a proximal shaft section 324 may be coupled together by pivotably interconnected interleaved flanges which are locked by a wing nut or other angle fixation means.

As further illustrated in FIGS. 1 and 2, shaft section 324 is provided with a plurality of apertures 325 which cooperate with a spring-loaded latch or detent element 326 on actuator component 318 in order to enable a user to adjust the distance between actuator 318 and shaft 310. Shaft section 326 thus serves in part as a length modification component for varying a distance of actuator 318 from shaft 310. Actuator 318 includes a projection 327 which is inserted into shaft section 324 in telescoping fashion. This length modification capability, particularly where device 308 is inserted through a laparoscopic cannula with one or more other laparoscopic instruments, serves to provide more space for the surgeon's hands.

Actuator 318 includes a pair of pivotably interconnected connected handle elements 328 and 330 and a knob 332 connected to distal end 312 of shaft 310 via at least one tension cable (not illustrated) for adjusting the orientation of the distal end of shaft 310 relative to the main length thereof. To this end, of course, the distal end of shaft 310 includes a flexible portion (not separately designated).

Figure 3:
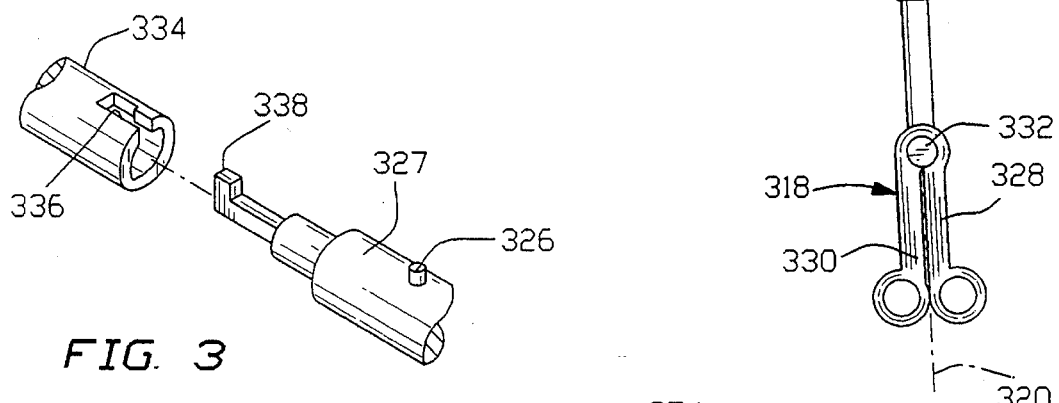
FIG. 3 is a partial schematic perspective view of a locking assembly in the device of FIGS. 2 and 3.

As illustrated in FIG. 3, surgical device 308 may be provided inside with a cable coupling 334 connected to the proximal end of a spring-loaded cable (not shown) which is connected at a distal end to operative tip 316. Coupling 334 is formed with an L-shaped slot 336 which receives an L-shaped locking element 338 located at the distal end of actuator projection 327. Coupling 334 and locking element 338 thus cooperate to form a force-transmitting connection for enabling the operation of surgical operating tip in response to a relative pivoting of handles 328 and 330. Spring-loaded latch or detent element 326 on actuator component 318 cooperates with an aperture 325 to lock actuator 318 to shaft section 324 and thence to shaft 310.

As noted above, device 308 may be inserted in parallel with another laparoscopic instrument through the same trocar sleeve or laparoscopic cannula into a patient's abdomen. Bendable connector element 322 and length modification component 324 enable a surgeon to adapt device 308 to provide greater maneuvering space for his or her hands at the proximal end of the laparoscopic cannula.

Figure 4:
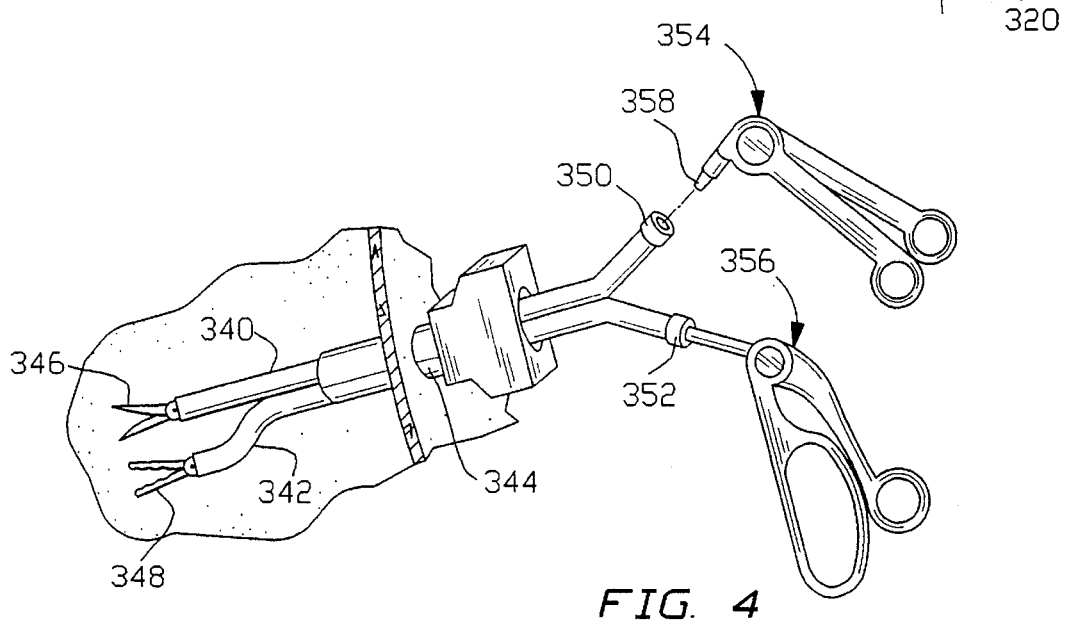
FIG. 4 is a schematic partial cross-sectional view of a patient's abdomen, showing use of another laparoscopic instrument or device in accordance with the present invention.

As illustrated in FIG. 4, one or more laparoscopic instrument shafts 340 and 342 inserted through a laparoscopic trocar sleeve 344 are provided at their distal ends with respective surgical tips 346 and 348 and at their proximal ends with couplings 350 and 352 for releasably or removably receiving respective actuators 354 and 356. Actuators 354 and 356 are provided with quick-release connectors 358 insertable into couplings 350 and 352 for establishing an operative connection to surgical tips 346 and 348. Upon removing an actuator 354 from its coupling 350, another actuator (not shown) of a different size, configuration or operative capability may be connected to shaft 340 via coupling 350. Of course, shafts 340 and 342 may be provided with bendable or pivotable couplings (see FIGS. 1 and 2) for enabling the adjustment of the orientation of actuators 354 and 356 with respective to shafts 340 and 342.

As illustrated in FIG. 5, a laparoscopic instrument assembly comprises a frame in the form of a rigid sleeve 12 and a pair of laparoscopic instruments 14 and 16 permanently inserted inside the sleeve. Each laparoscopic instrument 14 and 16 includes an operative tip 14a and 16a at a distal end, a shaft 14b and 16b, and an actuator 14c and 16c at a proximal end. Sleeve 12 has an outer diameter smaller than an inner diameter of a trocar sleeve or laparoscopic cannula (not shown), whereby a distal end portion of the instrument assembly may be inserted into a patient's abdomen through the laparoscopic cannula during a laparoscopic procedure. Laparoscopic instruments 14 and 16 may be used simultaneously (FIG. 5) or separately, in seriatum (FIG. 6).

Shafts 14b and 16b are slidably mounted to sleeve 12 for sliding motion relative thereto to enable adjustment in the location of the respective operative tips 14a and 16a relative to a surgical site. For instance, one or more instruments may be withdrawn or retracted so that the respective operative tips are spaced from the surgical site. More particularly, one or more of the laparoscopic instruments of the assembly may be shifted in the proximal direction so that the respective operative tips are retracted inside the distal end of the sleeve, thereby ensuring that those operative tips are not exposed for possible inadvertant contact with internal organic tissues of the patient.

Spring loaded locking pins 18 and 20 are provided on shafts 14b and 16b for cooperating with apertures 22 and 24 in sleeve 12 to alternately lock the respective shafts in a retracted neutral position and an extended use position. FIG. 5 shows both instruments 14 and 16 in an extended, use position relative to sleeve 12, while FIG. 6 shows instrument 14 shifted in a proximal direction relative to sleeve 12 to withdraw operative tip 14a into the distal end of sleeve 12, as indicated in dashed lines at 26. When both instruments 14 and 16 are being used, it may be desirable to lock only one of the instruments to sleeve 12 so that the instruments are slidable relative to one another, at least to a limited extent, for enhancing the modes of use of the instrument assembly.

Shafts 14b and 16b are flexible in a distal end region. Laparoscopic instruments 14 and 16 further comprise a bend control knob or knobs 14d and 16d operatively connected to the shafts 14b and 16b at a proximal end thereof for controlling the orientation of the respective shafts in their distal end regions. Ability to control the orientations of the distal ends of laparoscopic instruments 14 and 16 facilitates use of the instrument assembly of FIGS. 5 and 6. As depicted in FIG. 5, laparoscopic instruments 14 and 16 may be operated to have curved distal ends, whereby operative tip 14a and 16a approach a surgical site at respective angles relative to sleeve 12 and accordingly relative to a laparoscopic cannula through which the instrument assembly is inserted into a patient's abdomen.

As illustrated in FIG. 5, operative tips 14a and 16a are a scissors and a grasping forceps, respectively. However, it is to be noted that any combination of operative tips may be provided. Each operative tip 14a and 16a may be taken from the non-limiting group including biopsy forceps, graspers, trocars, suction devices, irrigators, scissors, cautery devices, staplers, suture applicators and clamps.

In using the laparoscopic instrument assembly of FIGS. 5 and 6, a laparoscopic cannula is first inserted in a patient's abdominal wall by a conventional laparoscopic procedure. Upon such disposition of the cannula, distal end portion of the laparoscopic instrument assembly is inserted through the cannula so that sleeve 12, as well as shafts 14b and 16b longitudinally traverse the cannula. During insertion of the instrument assembly, the distal end portions of shafts 14b and 16b are maintained in a straightened configuration. In addition, the laparoscopic instruments 14 and 16 may be shifted so that operative tips 14a and 16a are retracted into the distal end of sleeve 12.

Upon insertion of the laparoscopic instrument assembly through the cannula so that the distal end of the assembly is disposed inside the patient's abdomen, the operator manipulates actuator 14c and/or 16c to operate the respective surgical tip 14a and/or 16a. Generally, one actuator 14c or 16c will be manipulated prior to the other, although eventually the operating surgeon will have a hand on each actuator 14c and 16c during a portion of a laparoscopic surgical procedure. If necessary, locking pin 18 and/or 20 is removed from aperture 22 and/or 24 prior to manipulation of actuator 14c and/or 16c to enable an adjustment of the position of the respective laparoscopic instrument 14 and/or 16 relative to sleeve 12. During the manipulation of actuators 14c and 16c, sleeve 12 is maintained in a position longitudinally traversing the laparoscopic cannula or trocar sleeve in the patient's abdominal wall.

Other locking pins (not illustrated) may be provided on laparoscopic instruments 14 and 16 and sleeve 12 for enabling the entrainment of the sleeve to one or more of the instrument shafts 14b or 16b during a laparoscopic surgical procedure. In particular, locking elements are advantageously provided for fixing each laparoscopic instrument 14 and 16 to sleeve 12 in the extended positions of the instruments illustrated in FIG. 5. It is to be noted that essentially any type of mechanism may be provided to lock laparoscopic instruments 14 and 16 to sleeve 12.

Because instrument shafts 14b and 16b are flexible at a distal end, the distal end orientations of shafts 14b and 16b may be adjusted via knobs 14d and 16d prior to the manipulation of the respective actuators 14c and 16c.

At their proximal ends, shafts 14b and 16b are connected to actuators 14c and 16c via respective bendable or pivotable couplings 14e and 16e, which serve to provide adjustability with respect to the distance between actuators 14c and 16c. Couplings 14e and 16e may take any form described hereinabove with respect to coupling 322 of FIGS. 1 and 2 or any other equivalent coupling. It is to be noted, moreover, that handles 14c and 16c may be removably attached to shafts 14b and 16b, for example, as described hereinabove with reference to FIGS. 1 and 2 or FIG. 4.

As illustrated in FIG. 7, a modified laparoscopic instrument assembly comprises a rigid sleeve 32 and three laparoscopic instruments 34, 35, 36 inserted inside the sleeve. Each laparoscopic instrument 34, 35, 36 includes an operative tip 34a, 35a, 36a at a distal end, a central shaft 34b, 35b, 36b, and an actuator 34c, 35c, 36c at a proximal end. Sleeve 32 has an outer diameter smaller than an inner diameter of a trocar sleeve or laparoscopic cannula (not shown), whereby a distal end portion of the instrument assembly may be inserted into a patient's abdomen through the laparoscopic cannula during a laparoscopic procedure. Laparoscopic instruments 34, 35, 36 may be used simultaneously (FIG. 5) or separately, in seriatum (FIG. 6). Generally, one instrument 34, 35 or 36 is manipulated before the others at the onset of a laparoscopic surgical procedure, inasmuch as the surgeon's attention is directed to operating and placing the instruments in seriatum. In any event, at some time during the procedure, one actuator 34c, 35c or 36c will be manipulated and then subsequently a different actuator 34c, 35c or 36c will be operated. However, the surgeon may maintain his hands on two instruments during the entire procedure.

Shafts 34b, 35b, 36b are slidably mounted to sleeve 32 for sliding motion relative thereto to enable adjustment in the location of the respective operative tips 34a, 35a, 36a relative to a surgical site. For instance, one or more instruments 34, 35, 36 may be withdrawn or retracted so that the respective operative tips 34a, 35a, 36a are spaced from the surgical site. More particularly, one or more instruments 34, 35, 36 may be shifted in the proximal direction so that the respective operative tips 34a, 35a, 36a are retracted inside the distal end of sleeve 32, thereby ensuring that those operative tips are not exposed for possible inadvertant contact with internal organic tissues of the patient.

Spring loaded locking pins 38 are provided on shafts 34b, 35b, 36b for cooperating with apertures 42 in sleeve 32 to alternately lock the respective shafts in a retracted neutral position and an extended use position. Shafts 34b, 35b, 36b are flexible in a distal end region. Laparoscopic instruments 34, 35, 36 further comprise a bend control knob or knobs 34d, 35d, 36d operatively connected to the shafts 34b, 35b, 36b at a proximal end thereof for controlling the orientation of the respective shafts in their distal end regions. As depicted in FIG. 7, laparoscopic instruments 34, 35, 36 may be operated to have curved distal ends, whereby operative tip 34a, 35a, 36a approach a surgical site at respective angles relative to sleeve 32 and accordingly relative to a laparoscopic cannula through which the instrument assembly is inserted into a patient's abdomen.

As illustrated in FIG. 7, operative tips 34a, 35a, 36a are scissors, a hook and clamping forceps, respectively. However, it is to be noted that any combination of operative tips may be provided. Each operative tip 34a, 35a, 36a may be taken from the non-limiting group including biopsy forceps, graspers, trocars, suction devices, irrigators, scissors, cautery devices, staplers, suture applicators and clamps.

At their proximal ends, one or more shafts, e.g., shafts 34b and 36b, are connected to their actuators 34c and 36c via respective bendable or pivotable couplings 34e and 36e. Couplings 34e and 36e may take any form described hereinabove with respect to coupling 322 of FIGS. 1 and 2 or of any other equivalent coupling. It is to be noted, moreover, that handles 34c, 35c and 36c may be removably attached to their respective shafts 34b, 35c and 36b.

The operation of the laparoscopic instrument assembly of FIG. 7 is essentially the same as the operation of the instrument assembly of FIGS. 5 and 6. It is to be noted that one instrument 34, 35, 36 may remain in place without manipulation of the respective actuator 34c, 35c, 36c. For example, clamping forceps 36c may remain attached to an organ while the surgeon is manipulating actuators 35c and 36c to control the operation of scissors 34a and hook 35a. Alternatively, a non-used instrument 34, 35, 36 may be retracted to a storage position inside sleeve 32.

Figure 8:
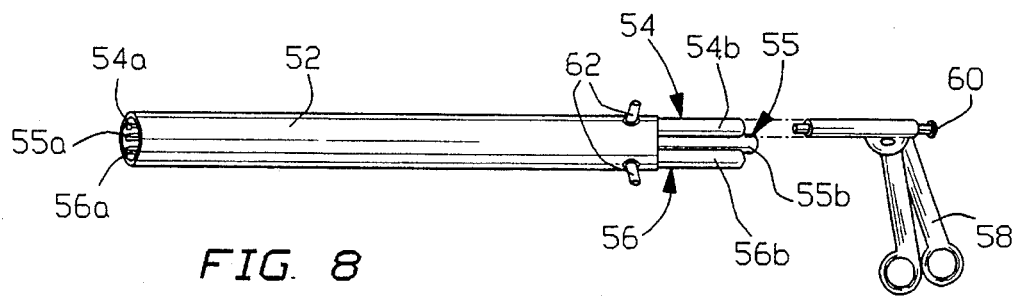
FIG. 8 is an exploded schematic perspective view, on a reduced scale, of yet another laparoscopic instrument or device.
Figure 9:
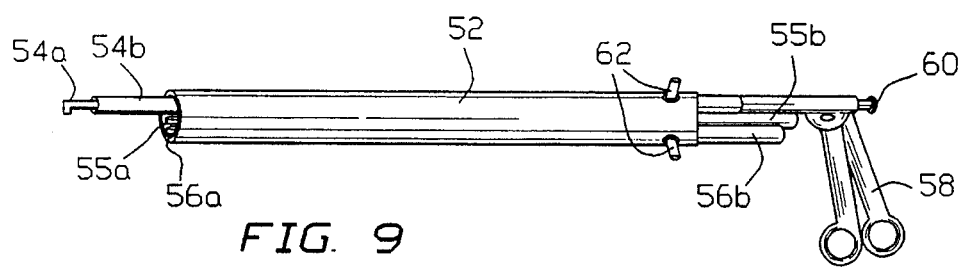
FIG. 9 is a schematic perspective view of the laparoscopic instrument assembly of FIG. 8, showing the assembly in one of several operational configurations.

As illustrated in FIGS. 8 and 9, another laparoscopic instrument assembly comprises a rigid sleeve 52 and a plurality of laparoscopic instrument shafts 54b, 55b, 56b inserted inside sleeve 52. Sleeve 52 has an outer diameter smaller than an inner diameter of a laparoscopic cannula, whereby a distal end portion of the instrument assembly may be inserted into a patient's abdomen through the laparoscopic cannula during a laparoscopic procedure. A hook 54a, scissors 55a, and grasping forceps 56a are operatively connected to respective shafts 54b, 55b, 56b at distal ends thereof, while an actuator component 58 is removably connectable successively to the different shafts 54b, 55b, 56b at a proximal end of sleeve 52 for independently actuating operative tips 54a, 55a, 56a.

Shafts 54b, 55b, 56b are slidably mounted to sleeve 52 for shifting instruments 54, 55, 56 between a retracted or storage position (FIG. 8) and an extended or use position (see instrument 54 in FIG. 9). In a preferred method of using the instrument assembly of FIGS. 8 and 9, only one instrument 54, 55, 56 at a time is shifted into the extended or use position, as shown in FIG. 9. However, particularly if shafts 54b, 55b, 56b are provided with controllably flexible distal end portions, it may be possible to operate one instrument 54, 55, 56 while another is extended. For example, grasping forceps 56a may be left grasping internal tissues of a patient while actuator component or handle 58 is removed from shaft 56b and connected to the proximal end of shaft 55b for manipulating scissors 55a.

Prior to the extension of the respective instrument, for example, instrument 54, actuator component or handle 58 is attached to the proximal end of instrument shaft 54b, as shown in FIG. 9. Actuator component 58 is provided with a latch or detent 60 for locking the actuator component to any one of the shafts 54*b*, 55*b*, 56*b*.

In using the instrument assembly of FIGS. 8 and 9, multiple laparoscopic instruments 54, 55, 56 are simultaneously inserted through a single trocar sleeve or laparoscopic cannula. To change from one instrument 54, 55, 56 to another, the surgeon simply disconnects actuator component or handle 58 from the shaft 54*b*, 55*b*, 56*b* of one instrument 54, 55, 56 and connects it to the shaft of another instrument. Of course, the first instrument may be retracted into sleeve 52 prior to the extension of the other.

Locking pins 62 may be provided for alternately locking shafts 54*b*, 55*b*, 56*b* in a retracted neutral position and an extended use position.

Of course, the operative tips 54*a*, 55*a*, 56*a* may have different structures, for performing different surgical operations.

Figure 10:
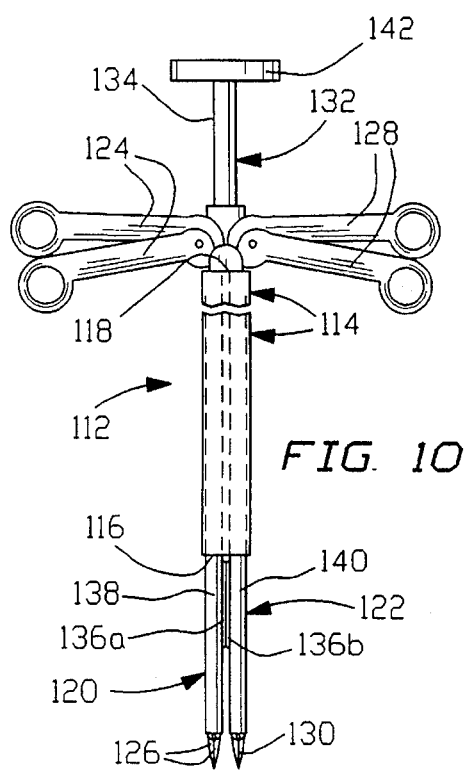
FIG. 10 is a schematic side elevational view of a laparoscopic surgical clamping assembly, showing a pair of grasping forceps disposed in a mutually parallel insertion configuration and with closed grasping jaws.
Figure 11:
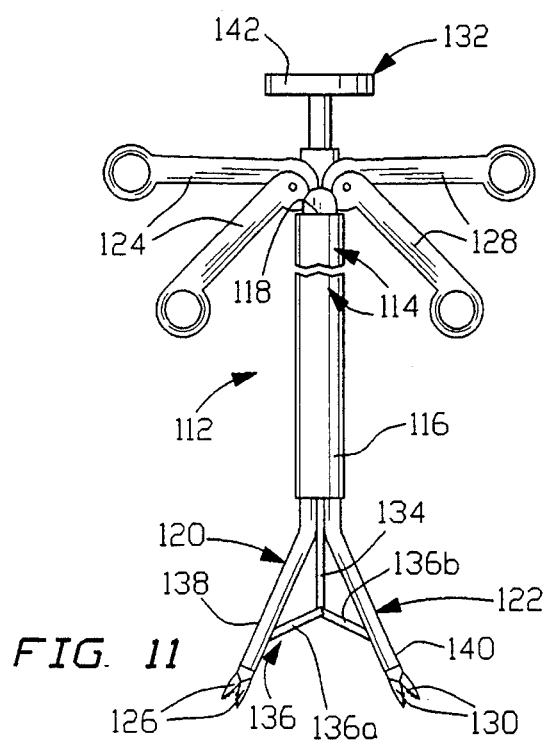
FIG. 11 is a schematic side elevational view of the laparoscopic surgical clamping assembly of FIG. 1, showing the grasping forceps disposed in a spread-apart use configuration and with opened grasping jaws.

As illustrated in FIGS. 10 and 11, a surgical clamping device 112 for spreading or stretching clamped organic tissues comprises a frame member 114 having a distal end 116 and a proximal end 118. Two clamping or holding mechanisms in the form of respective grasping forceps 120 and 122 are movably mounted to frame member 114 at distal end 116 thereof for exerting clamping forces to hold spaced organic tissues of a patient. A first actuator 124 is mounted to frame member 114 at proximal end 118 thereof and is operatively connected to grasping forceps 120 for controlling the opening and closing of jaws 126 of that forceps, while a second actuator 128 is mounted to frame member 114 at proximal end 118 and is operatively connected to grasping forceps 122 for alternately opening and closing jaws 130 of that grasping forceps. A third actuator 132 including a reciprocatable plunger element or push rod 134 is slidably mounted to frame member 114 and operatively connected to grasping forceps 120 and 122 for increasing the distance between jaws 126 and jaws 130, thereby stretching the clamped organic tissues and facilitating access to the stretched tissues.

As shown in FIG. 11, actuator 132 also includes an articulated linkage 36 comprising a pair of arms 136*a* and 136*b* pivotably connected to push rod 134 at the distal end thereof and pivotably connected to shafts 138 and 140 of respective grasping forceps 120 and 122. Shafts 138 and 140 are flexible in a region immediately distal of a distal end of frame member 114, thereby enabling a relative spreading of grasping forceps 120 and 122 from a straightened or mutually parallel insertion configuration of FIG. 10 to a spread use configuration if FIG. 11 upon a distally directed stroke of push rod 134. Push rod 134 is provided at a proximal end with a flange 142 for facilitating manual reciprocation of push rod 134.

Figure 12A:
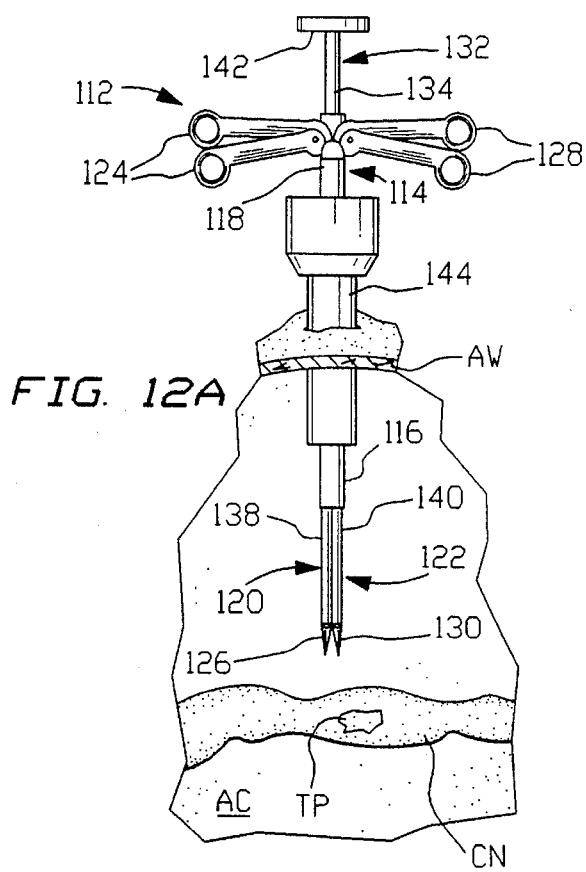
FIGS. 12A–12C are partial schematic cross-sectional views of a patient's abdomen with the surgical clamping assembly of FIGS. 1 and 2 inserted therein, the clamping assembly being illustrated in successive steps of a clamping and spreading operation in accordance with the present invention.
Figure 12B:
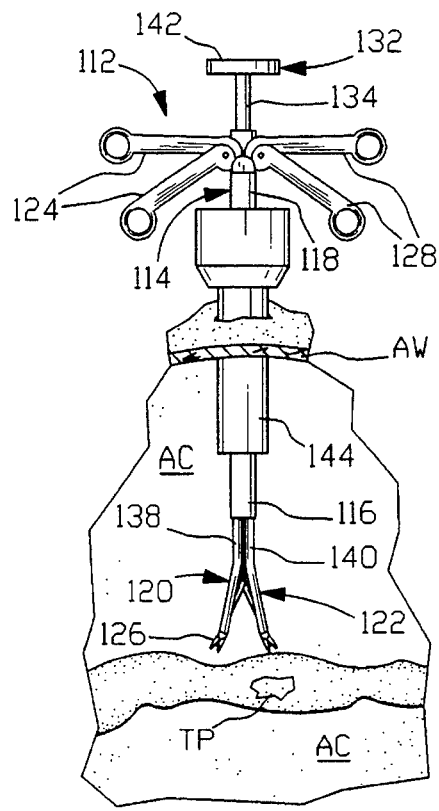
Figure 12C:
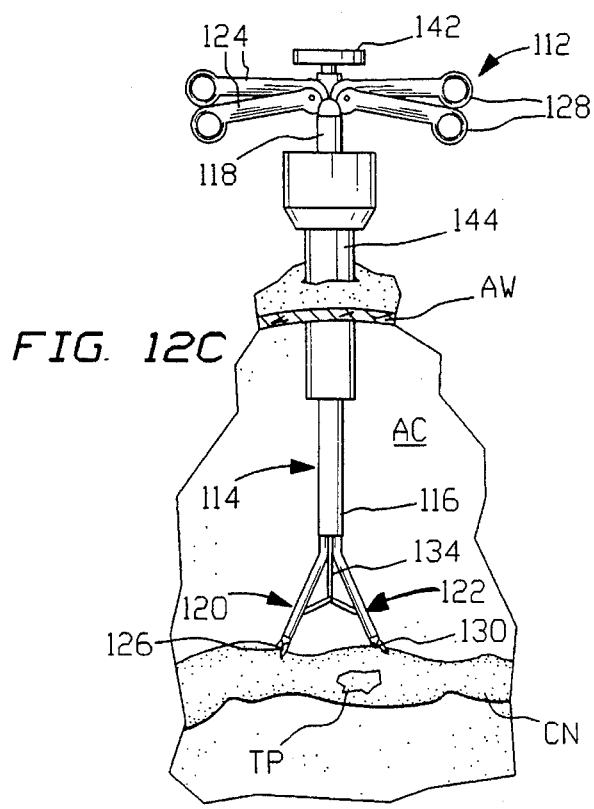

FIGS. 12A–12C show a distal end portion of clamping device 112 inserted into an abdominal cavity AC of a patient through a laparoscopic trocar sleeve 144 itself traversing an abdominal wall AW of the patient. FIG. 12A illustrates an initial insertion configuration of clamping device 110 wherein push rod 134 is retracted in a proximal direction and grasping jaws 126 and 130 are closed. (This configuration is also used when the clamping device 112 is being withdrawn from abdominal cavity AC upon termination of the laparoscopic tissue spreading operation.)

Upon the insertion of the distal end portion of clamping device 112 into abdominal cavity AC, push rod 134 may be shifted slightly in the distal direction, if desired, to partially separate jaws 126 and 130 of grasping forceps 120 and 122 (FIG. 12B). Actuators 124 and 128 are then operated to open jaws 126 and 130, Whereupon device or instrument 112 is manipulated from outside the patient to grasp respective portions of organic tissue, for example, of the colon CN, on opposite sides of a traumatic injury or perforation TP. After a subsequent closure of jaws 136 and 130, push rod 134 is pushed further in the distal direction, as depicted in FIG. 12C, to spread the tissues of colon CN in the region about traumatic injury or perforation TP.

The stretching of the tissues of colon CN about perforation TP facilitates surgery by providing direct access to the injury. A suturing operation or other surgical treatment may be performed easily on traumatic perforation TP. Upon the closure of perforation TP, the steps illustrated in FIGS. 12A–12C are performed in reverse order.

As illustrated in FIG. 13, another surgical clamping device 152 for spreading or stretching clamped organic tissues comprises a frame member 154 having a distal end 156 and a proximal end (not shown). Two clamping or grasping forceps 160 and 162 are movably mounted to frame member 154 at distal end 156 thereof for exerting clamping forces on spaced organic tissues of a patient. Actuators (not shown) are mounted to frame member 154 at the proximal end thereof for controllably opening and closing jaws 166 of forceps 160 and closing jaws 168 of forceps 162. A third actuator includes a rotatable shaft 170 carrying a tapered screw 172 at a distal end. Upon a rotation of shaft 170, screw 172 is pulled into an internally threaded split bushing or nut 174. Nut 174 has a first half 174*a* attached to a partially flexible shaft 176 of forceps 160, while a second half 174*b* of nut 74 is fixed to a partially flexible shaft 178 of forceps 162. The entry of screw 172 into nut 174 causes the separation of halves 174*a* and 174*b* and consequently of forceps shafts 176 and 178 in opposition to an inherent spring force or a helical tension spring 180 extending between forceps shafts 176 and 178.

As illustrated in FIG. 14, yet another surgical clamping device 182 for spreading or stretching clamped organic tissues comprises a frame member 184 having a distal end 186 and a proximal end (not illustrated). Two clamping or grasping forceps 190 and 192 are movably mounted to frame member 184 at distal end 186 thereof for exerting clamping forces on spaced organic tissues of a patient. Actuators (not shown) are mounted to frame member 184 at the proximal end thereof for controllably opening and closing jaws 194 of forceps 190 and closing jaws 196 of forceps 192. A third actuator includes a slidable shaft 198 carrying a wedge 1100 at a distal end. Upon a sliding of shaft 198 in the distal direction, wedge 200 slidingly engages camming elements 202 and 204 which are attached to shafts 206 and 208 of forceps 192 and 194 and forces the shafts apart in opposition to an inherent spring force or a helical tension spring 210 extending between forceps shafts 206 and 208.

As depicted in FIG. 15, any of the surgical clamping devices described above with reference to FIGS. 10–14 may be provided at the proximal ends of the respective grasping forceps 120 and 122, 160 and 162, 190 and 192 with bendable or pivotable couplings 212 and 214, as described hereinabove with reference to numerical designation 322 (FIGS. 1 and 2). It is to be noted, moreover, that actuators 124 and 128 may be removably attached to their respective shafts for enabling the substitution of differently configured or differently operating handles. Also length modification components (see discussion above with respect to reference numerals 324 and 326) may be provided on any of the laparoscopic surgical instruments described herein.

Although the invention has been described in terms of particular embodiments and applications, one of ordinary skill in the art, in light of this teaching can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A surgical device comprising:

a frame member having a distal end and a proximal end;

first holding means secured to said frame member and disposed at said distal end thereof for securing a hold on first organic tissues of a patient;

second holding means secured to said frame member and disposed at said distal end thereof for securing a hold on second organic tissues of the patient spaced from the first organic tissues, at least one of said first holding means and said second holding means being movable relative to the other;

first actuator means, mounted to said frame member at said proximal end thereof and operatively connected to said first holding means, for controlling operation of said first holding means;

second actuator means, mounted to said frame member at said proximal end thereof and operatively connected to said second holding means, for controlling operation of said second holding means; and additional actuator means, operatively independent of said first actuator means and said second actuator means and mounted to said frame member and operatively connected to said first holding means and said second holding means, for moving at least one of said first holding means and said second holding means relative to the other, thereby enabling a stretching of third organic tissues between said first organic tissues and said second organic tissues and facilitating access to said third organic tissues.

2. The device defined in claim 1 wherein said frame member is elongate and sufficiently thin to fit down a laparoscopic trocar sleeve.

3. The device defined in claim 1 wherein said first holding means and said second holding means are secured to said frame means via respective flexible shafts, said additional actuator means including an articulated linkage pivotably connected to said shafts, said third actuator means further including means for alternately shifting said linkage in a distal direction and a proximal direction.

4. The device defined in claim 1 wherein said additional actuator means includes an articulated linkage.

5. The device defined in claim 1 wherein said additional actuator means includes a screw mechanism.

6. A surgical method comprising the steps of:

providing a surgical instrument with an elongate shaft having first holding means and second holding means at a distal end for independently securing holds on respective organic tissues and actuator means at a proximal end for operating said first holding means and said second holding means;

inserting a distal end portion of said instrument through a laparoscopic trocar sleeve into a patient;

upon insertion of said distal end portion of said instrument through said trocar sleeve, securing holds on selected first organic tissues and selected second organic tissues about an operative site with said first holding means and said second holding means, respectively;

upon securing holds on said selected first organic tissues and said selected second organic tissues with said first holding means and said second holding means, operating said actuator means to move one of said first holding means and said second holding means relative to the other of said first holding means and said second holding means to stretch third organic tissues between said first organic tissues and said second organic tissues; and upon stretching of said third organic tissues, performing an operation at said surgical site.

7. The method defined in claim 6 wherein said step of holding includes the step of clamping said selected organic tissues with said first means and said second means.

* * * * *